US 6,671,547 B2

(12) United States Patent
Lyster et al.

(10) Patent No.: US 6,671,547 B2
(45) Date of Patent: Dec. 30, 2003

(54) ADAPTIVE ANALYSIS METHOD FOR AN ELECTROTHERAPY DEVICE AND APPARATUS

(75) Inventors: Thomas D. Lyster, Bothell, WA (US); Carlton B. Morgan, Bainbridge Island, WA (US); Gust H. Bardy, Seattle, WA (US); Bradford E. Gliner, Sammanush, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 205 days.

(21) Appl. No.: 09/879,057

(22) Filed: Jun. 13, 2001

(65) Prior Publication Data
US 2002/0193848 A1 Dec. 19, 2002

(51) Int. Cl.$^7$ ................................................ A61N 1/39
(52) U.S. Cl. .................................. 607/6; 607/5; 607/62
(58) Field of Search ................................ 607/4–6, 9, 62

(56) References Cited

U.S. PATENT DOCUMENTS

| | | | |
|---|---|---|---|
| 5,421,830 A | 6/1995 | Epstein et al. | 607/30 |
| 5,593,427 A | 1/1997 | Gliner et al. | 607/7 |
| 5,607,454 A | 3/1997 | Cameron et al. | 607/5 |
| 5,683,424 A * | 11/1997 | Brown et al. | 607/5 |
| 5,735,879 A | 4/1998 | Gliner et al. | 607/7 |
| 5,836,993 A | 11/1998 | Cole | 607/59 |
| 5,843,134 A | 12/1998 | Thong et al. | 607/17 |
| 5,879,374 A | 3/1999 | Powers et al. | 607/5 |
| 5,928,269 A * | 7/1999 | Alt | 607/5 |
| 5,951,484 A | 9/1999 | Hoium et al. | 600/515 |
| 5,987,356 A | 11/1999 | DeGroot | 607/5 |
| 6,021,349 A * | 2/2000 | Arand et al. | 607/5 |
| 6,181,966 B1 | 1/2001 | Nigam | 607/4 |

FOREIGN PATENT DOCUMENTS

WO   WO9924114   5/1999   ........... A61N/1/39

\* cited by examiner

*Primary Examiner*—Carl Layno

(57) ABSTRACT

An electrotherapy device including at least one sensor operable to sense at least one physiological parameter of a patient. A controller is operably connected to the at least one sensor operable to receive signals from the at least one sensor corresponding to the at least one physiological parameter. Memory is operable to store computer-programming code executed by the controller. The programming code includes decision-making criteria operable to adapt a patient treatment in response changes to the detected at least one physiological parameter. At least one pair of electrodes is operably connected to the controller and operable to administer the treatment to the patient.

17 Claims, 3 Drawing Sheets

ADAPTIVE ANALYSIS METHOD FOR AN ELECTROTHERAPY DEVICE AND APPARATUS

BACKGROUND OF THE INVENTION

1. Field of the Invention

This invention relates generally to an electrotherapy device. Specifically, this invention relates to a method and apparatus for analyzing a post-shock rhythm of a patient being treated by an electrotherapy device and using the results of the post-shock rhythm analysis to make a decision about patient treatment. Electrotherapy devices include defibrillators, cardioverters and training devices that simulate the operation of an electrotherapy device. Defibrillators include automatic or semi-automatic external defibrillators (AEDs).

2. Description of the Prior Art

Electrotherapy devices are used to provide electric shocks to treat patients for a variety of heart arrhythmias. For example, external defibrillators typically provide relatively high-energy shocks to a patient (as compared to implantable defibrillators), usually through electrodes attached to the patient's torso. External defibrillators are used to convert ventricular fibrillation ("VF") or shockable ventricular tachycardia ("VT") to a normal sinus rhythm. Similarly, external cardioverters can be used to provide paced shocks to convert atrial fibrillation ("AF") to a more normal heart rhythm.

Sudden cardiac arrest ("SCA") is the leading cause of death in the United States. On average, 1000 people per day die; this translates into one death every two minutes. Most SCA is caused by VF, in which the heart's muscle fibers contract without coordination, thereby interrupting normal blood flow to the body. The only effective treatment for VF is electrical defibrillation, which applies an electric shock to the patient's heart. The electric shock clears the heart of the abnormal electrical activity (in a process called "defibrillation") by depolarizing a critical mass of myocardial cells to allow spontaneous organized myocardial depolarization to resume.

To be effective, the defibrillation shock must be delivered to the patient within minutes of the onset of VF. Studies have shown that defibrillation shocks delivered within one minute after the onset of VF achieve up to a 100% survival rate.

However, the survival rate falls to approximately 30% after only 6 minutes. Beyond 12 minutes, the survival rate approaches zero. Importantly, the more time that passes, the longer the brain is deprived of oxygen and the more likely that brain damage will result. As improved access to defibrillators increases, survival rates from SCA also increase.

AEDs typically use algorithms to determine whether or not a shock should be delivered to a patient. Numerous algorithms and programmable systems are known for recording and analyzing a patient's cardiac signal. For example, U.S. Pat. No. 5,421,830, to Epstein et al. for "Programming System Having Means for Recording and Analyzing a Patient's Cardiac Signal," the specification of which is incorporated, teaches one programming system for detecting an arrhythmia. The programming system is implemented in a manner that enables optimization of the settings of various rhythm detection criteria and/or parameters relating to hemodynamic performance which are programmed into an implanted cardiac stimulating device ("ICD"). U.S. Pat. No. 5,951,484 to Houim et al. for "Method of Non-Invasively Determining a Patient's Susceptibility to Arrhythmia," discloses a method of using biased and unbiased QRS complexes to detect the patient's susceptibility to an arrhythmia.

The algorithms used by AEDs typically do not rely on patient pulse information, since pulse information is not obtainable through the electrode pads used by the AED and information supplied by the user may or may not be accurate. Failure to use pulse information in determining whether to shock a patient can result in a no-shock decision for a potentially shockable rhythm. This is because AEDs are designed to make shock decisions conservatively. AEDs also analyze electrocardiogram (ECG) data segments received from a patient in isolation from prior analysis results or protocol events.

Notwithstanding the great strides made in developing AED patient analysis systems, improvements are still possible that would improve the efficacy of the treatment and decision making by the AED algorithm assessing patient treatment. What is needed, therefore, is a method of evaluating patient ECG that improves patient treatment.

SUMMARY OF THE INVENTION

The present invention includes an electrotherapy device. At least one sensor is operable to sense at least one physiological parameter of a patient. A controller is operably connected to the at least one sensor operable to receive signals from the at least one sensor corresponding to the at least one physiological parameter. Memory is operable to store computer-programming code executed by the controller. The programming code includes decision-making criteria operable to adapt a patient treatment in response changes to the detected at least one physiological parameter. At least one pair of electrodes is operably connected to the controller and operable to administer the treatment to the patient.

The present invention also concerns an electrotherapy device that includes at least one sensor operable to sense at least one physiological parameter of a patient. A circuit is operably connected to the sensor and configured to detect a patient physiological parameter. A controller is operably connected to the circuit and operable to receive signals from the circuit corresponding the to at least one physiological parameter. The controller is configured to implement decision-making criteria responsive to changes in the measured parameter values, and operative to adapt patient treatment based upon the decision-making criteria.

Additionally, the present invention relates to a method for performing electrotherapy. The method includes detecting at least one physiological parameter of a patient. The at least one physiological parameter is analyzed. A patient treatment is adapted in response to changes in the detected at least one physiological parameter. The treatment is administered to the patient.

Furthermore, the present invention provides a method for performing electrotherapy on a patient. The method includes an operator of an electrotherapy device administering to a patient based upon instructions produced by the electrotherapy device and adapting the instructions produced by the electrotherapy device based upon detected changes in at least one physiological parameter of the patient in response to prior treatment administered to the patient with the electrotherapy device.

An electrotherapy device is disclosed. The electrotherapy device includes a sensor, a controller coupled to the sensor and configurable to detect cardiac signals, and memory having computer programming code stored in the memory.

The computer programming code is executed in the controller and has decision-making criteria that, in response to previously detected cardiac signals, may adapt patient treatment. The computer programming code may further include decision-making criteria. The decision-making criteria can operate to adapt patient treatment by generating a shock/no-shock decision or it may adapt patient treatment by generating a therapy decision. A user interface may be provided that is coupled with the controller. The user interface would enable a user to adapt the decision-making criteria of the computer-programming algorithm. The user interface could include, for example, a tactile input device associated with the device. The decision-making criteria are optimized to utilize patient physiological parameters in making its decision. Patient physiological parameters include, for example, heart rate, conduction variable and stability variable, to name a few. Typically, the device will analyze cardiac signal such as, ECG parameters, heart rate, conduction variable and stability variable. The computer programming code is typically executed in the controller to recommend alternative patient therapies based on prior patient events and/or arrhythmia analysis algorithm decisions.

An electrotherapy device may also include a sensor and a circuit coupled to the sensor. The circuit is configured to detect a patient physiological parameter. The device may also include a controller coupled with the circuit, configured to implement decision-making criteria responsive to the measured parameter values and operative to adapt patient treatment based upon the decision-making criteria. Patient physiological parameters typically include ECG parameters, heart rate parameters, heart conduction variables, and heart stability variables, blood pressure, $SPO_2$, and any other suitable physiological parameters. The decision-making criteria utilize patient physiological parameters, including prior decision making results, to determine the appropriate therapy to administer. From this information, the decision-making criteria generate a shock/no shock decision, or generate a therapy decision (for instance, a decision to administer appropriate pharmaceutical agents).

A method for performing electrotherapy can include providing a circuit and a sensor operable to detect a patient physiological parameter, and control circuitry. The control circuitry can implement decision-making criteria operable to adapt treatment based upon the decision-making criteria and detect the patient physiological parameter. The control circuitry can also analyze the patient physiological parameter and determine whether a prior patient physiological parameter has been analyzed. If a prior patient physiological parameter has been analyzed the prior patient physiological parameter is analyzed in conjunction with the analyzed patient physiological parameter. A treatment decision is made based on the evaluation. If a prior patient physiological parameter has not been analyzed, the analyzed patient physiological parameter is analyzed and a treatment decision is made based on the evaluation. The circuitry can also cause treatment to be delivered to the patient. As described above, patient physiological parameter include, for example, ECG segment comprises analyzing at least one of heart rate, heart condition and heart stability, blood pressure, and SPO2, to name a few. Causing therapy to be delivered may also include enabling shock delivery to a patient with the adapted control circuitry based upon known prior analysis results. The sensor may be a patient electrode and the circuit may be a cardiac event detection system.

Still other objects and advantages of the present invention will become readily apparent by those skilled in the art from a review of the following detailed description. The detailed description shows and describes preferred embodiments of the present invention, simply by way of illustration of the best mode contemplated of carrying out the present invention. As will be realized, the present invention is capable of other and different embodiments and its several details are capable of modifications in various obvious respects, without departing from the invention. Accordingly, the drawings and description are illustrative in nature and not restrictive.

BRIEF DESCRIPTION OF THE DRAWINGS

Objects and advantages of the present invention will be more clearly understood when considered in conjunction with the accompanying drawings, in which.

DESCRIPTION OF THE PREFERRED EMBODIMENTS

Figure 1:
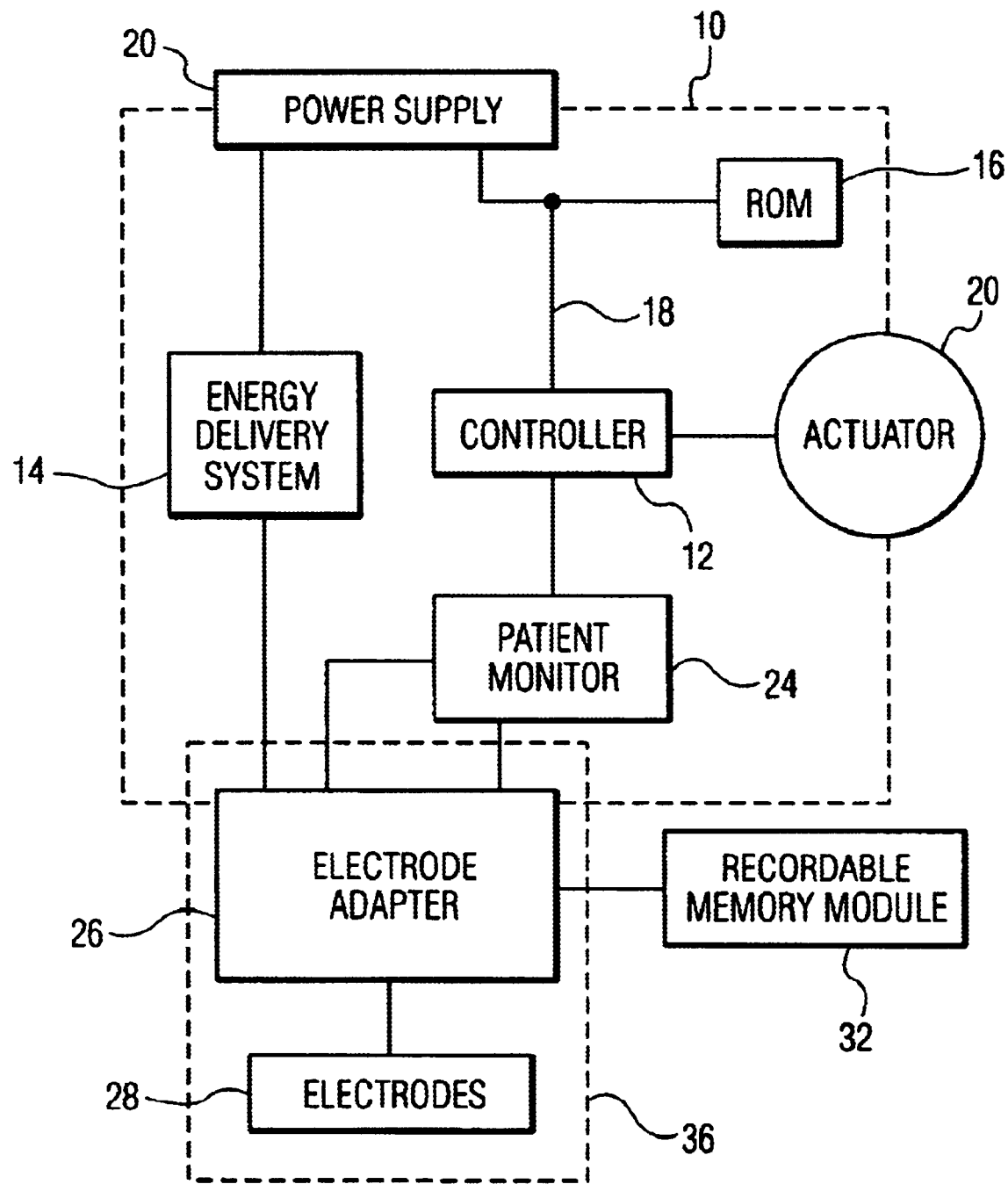
FIG. 1 represents a block diagram of an electrotherapy device showing a detachable electrode system.

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment shown, but is to be accorded the widest scope consistent with the principles and features disclosed herein.

An electrotherapy device according to the present invention includes at least one sensor operable to sense at least one physiological parameter of a patient. The physiological parameter could include an ECG parameter, heart rate parameter, heart condition, heart stability, blood pressure, $SPO_2$ and/or other parameter. If the physiological parameter is an ECG parameter, the parameter could include a conduction variable and/or stability variable. The sensor can include a heart rate sensor, respiration sensor, and/or any other sensor. Typically, the at least one sensor contacts some portion of the patient's body and produces signals corresponding to the at least one physiological parameter measured.

A controller is operably connected to the at least one sensor. The controller may include one or more processors, circuitry and other elements for controlling operation of at least the sensor(s). The controller is operable to receive the signals from the at least one sensor. The controller and the sensor(s) may be connected with lead wire(s) extending from the sensor(s) to the controller. Alternatively, the sensor(s) and the controller may be wirelessly connected, utilizing any suitable wireless communication protocol.

Memory is included in the device for storing computer-programming code executed by the controller. The programming code includes decision-making criteria operable to adapt a patient treatment in response to changes in the detected physiological parameter(s). The decision-making criteria may include decision trees that analyze the physiological parameter(s). The decision-making process can incorporate medical knowledge that a caregiver would utilize in caring for a patient in similar circumstances.

Along these lines, the decision making process can analyze the electrocardiogram signals received from the sensor(s) using a decision making process that a physician or an emergency medical technician would utilize in similar circumstances to administer to a patient. For example, the programming code can be executed in the computer to recommend alternative patient therapies based upon prior patient events and/or arrhythmia analysis. The prior patient events are events that have occurred as the patient is treated with the device. In this way, the present invention can adapt patient treatment during use of the device.

By accounting for changes and/or trends in changes in the physiological condition of the patient, the present invention can infer more than circumstances at any one moment would indicate. Along these lines, if a patient responds in a certain manner or does not respond, then the present invention can account for this and alter treatment. In this manner, the present invention functions differently from existing devices, which analyze a patient's condition at certain times, but which do not account for the results of prior analyses or prior treatments.

For example, a standardized treatment protocol may include delivering a shock to a patient every time that ventricular fibrillation (VF) is detected by an analysis of the patient's ECG. On the other hand, an instrument that implements the present invention may behave differently. According to one example, a patient has been shocked from VF to another ECG rhythm several times, but following each conversion, the patient nevertheless quickly relapses to VF. Based upon this history, a device according to the present invention may select an alternative treatment in an attempt to find a more effective treatment for VF in this patient. Alternative treatments could include longer intervals of CPR between shocks, or the application of an antiarrhythmic or a thrombolytic drug. By dealing with aggregated results, a history of decision-making criteria, the present invention can provide more effective treatment than known devices.

By including such programming software, the present invention can change the therapy protocol during treatment. Additionally, the present invention can account for limited knowledge and/or memory on the part of operators of the device. In the case of lay people operating the device, the device can instruct the person in administering to the patient. Even if the operator of the device is skilled, the present invention can account for gaps and/or lapses in knowledge.

As medical knowledge advances, the programming code can be updated to reflect the updated knowledge. Those of ordinary skill in the art would be able to generate computer-programming code that incorporates such medical knowledge and decision-making criteria without undue experimentation once aware of the disclosure contained herein.

In practice, the decision-making criteria can result in the processor generating treatment messages to an operator. Along these lines, the decision-making criteria can generate therapy decisions that a user will follow. For example, the decision-making criteria can generate a shock/no-shock message to an operator of the device.

The messages could be delivered to the operator in a written or audible form. Along these lines, the device may include a user interface operably connected with the controller. The user interface can permit the user to adapt the decision-making criteria of the programming code. For example, the user interface may include means, such as one or more tactile input devices, for the user to enter information regarding the patients that the decision-making criteria may utilize in analyzing the patient's condition. The tactile input devices could include one or more buttons or other elements. The user interface may also include a speaker and/or a display to send messages to the user, prompt the user for information, and/or deliver instructions to the user.

A device according to the present invention also includes at least one pair of electrodes for administering treatment to the patient. According to some embodiments, the sensors and the electrodes are the same. In other words, the same electrodes may be utilized to sense a patient's electrocardiogram signals and administer a defibrillating shock to the patient if needed. The sensors are operably connected to the controller, such as by leads connected to both elements. The controller will deliver defibrillation energy or other treatment to the patient when the decision making process indicates that treatment is required.

The following discussion describes in greater detail embodiments of the present invention. FIG. 1 is a block diagram showing a device 10. Device 10 is an electrotherapy device. The device 10 may include the ability to defibrillate, cardiovert, or pace a patient, or a combination of these features. Device 10 has a controller 12 that operates an energy delivery system 14 and performs other aspects of the operation of the device. Software instructions for operating the device are accessible from read only memory (ROM), such as incorporated ROM 16. The controller accesses instructions for operation from ROM 16. It should be understood that, in this and other embodiments described below, "controller" means a microprocessor, controller, gate array, other control logic, or any combination of these elements.

Controller 12 communicates with ROM 16 via a memory bus 18. A recordable memory module 32 is attached to device 10 via an electrode system 36, as shown in FIG. 1. Electrode system 36 includes electrodes 28 and an electrode adapter 26. Although it will be appreciated by a person of skill in the art that an adapter 26 is not required when the electrodes are connected directly to the defibrillator.

Electrode adapter 26 is connected to electrodes 28 and is removably connected to the device 10. A suitable electrode system 36 adaptable for use in this invention would be, for example, Heartstream ForeRunner® electrodes.

Electrodes 28 communicate with a patient monitor 24 via electrode adapter 26 to provide patient ECG data from the patient to the patient monitor 24. Electrodes include electrodes capable of delivering defibrillation, monitoring a patient condition, delivering pacing pulses, or a combination of those features. In an AED, the patient monitor 24 monitors the patient for a heart rhythm and subsequently determines whether the monitored rhythm is shockable.

When the rhythm is shockable, the patient monitor 24 then communicates a shock decision to the controller 12. The controller 12 then communicates to the energy delivery system 14. The energy delivery system 14 then delivers a therapeutic energy pulse to the patient (not shown) through electrodes 28 attached to the defibrillator 10 via electrode adapter 26, using the power supply 20 as the energy source.

Figure 2:
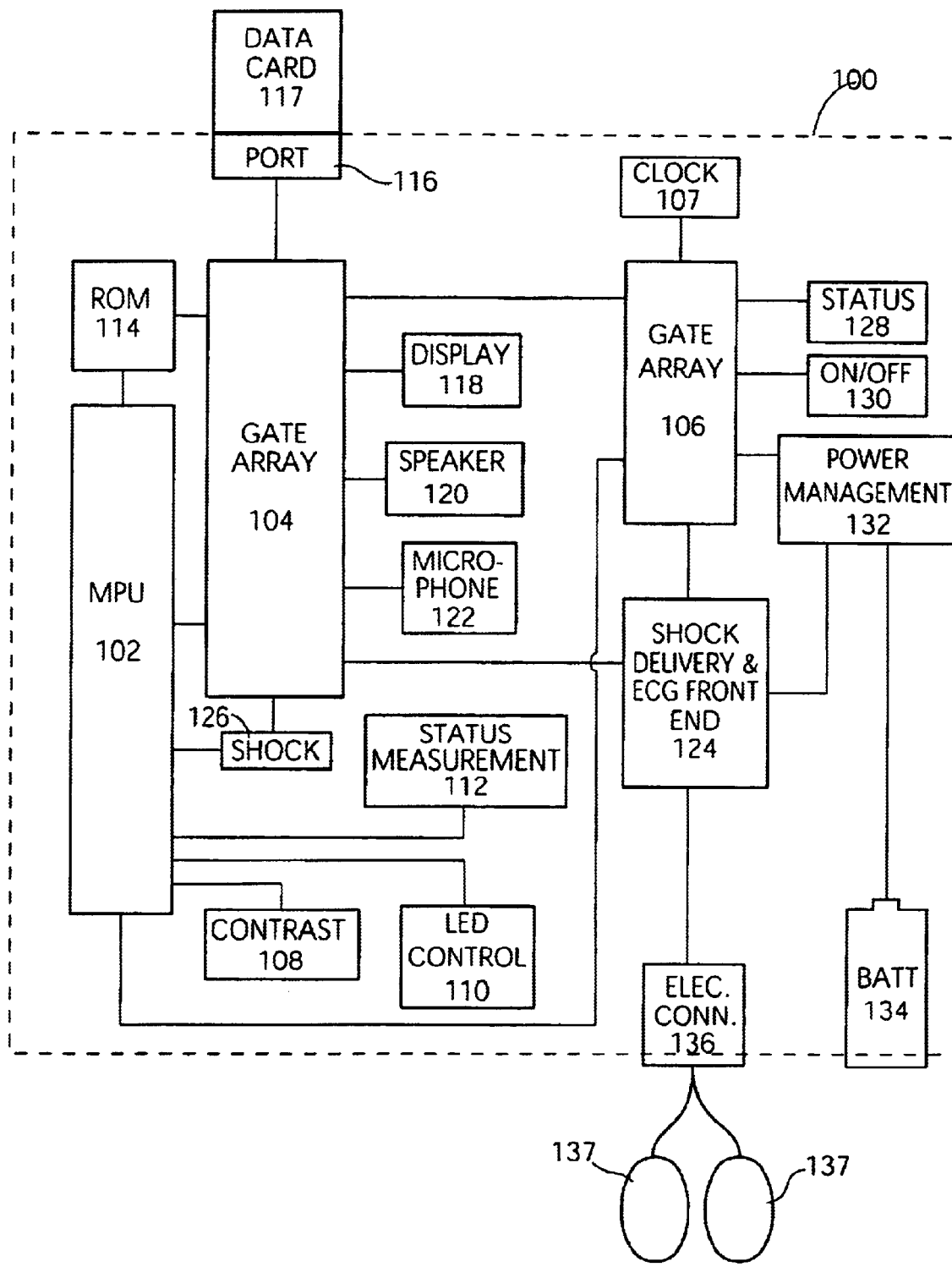
FIG. 2 represents a block diagram that shows the major components of a semi-automatic external defibrillator shown in FIG. 1.

The major components of an AED are shown in FIG. 2 in block diagram form. Further detailed information about the operation of an AED can be obtained in U.S. Pat. No. 5,836,993, to Cole for "Electrotherapy Device Control System and Method" and U.S. Pat. No. 5,593,427 to Gliner et al., for "Electrotherapy Method," the specifications of which are incorporated herein. As will be appreciated by those of skill in the art, the invention can be used in a variety of AEDs and is not limited to this configuration, which is used for illustration purposes only.

In this illustration, defibrillator control functions are divided among a microprocessor unit (MPU) 102 and two custom gate arrays 104 and 106.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112.

Gate array 104 implements the memory map to system ROM 114. System ROM 114 is preferably flash ROM, although EPROM or any other electrically erasable and programmable nonvolatile memory could be used. Gate array 104 also controls a display 118, a speaker 120, and a microphone 122. Gate array 104 can actuate a relay within the shock delivery and ECG front-end system 124 in response to actuation of a shock button 126 by a user during treatment mode.

Gate array 106 provides a system monitor function by performing automatic self-tests of the defibrillator and its components. The gate array 106 displays the operational status of the defibrillator on a status display 128. Details of suitable self-tests may be found in U.S. Pat. No. 5,879,374, to Powers, et al. for "External Defibrillator with Automated Self-Testing Prior to Use," the entire contents of the specification of which is incorporated herein by reference.

Gate array 106 is also the defibrillator's interface with a user-activated on/off switch 130. Gate array 106 controls the power management subsystem 132 to provide power to operate system components from power supply 134 and to provide energy to the shock delivery system's capacitor(s) for a therapeutic shock during treatment mode. Gate array 106 also interfaces with the defibrillator's ECG front end, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No. 5,735,879 to Gliner et al. for "Electrotherapy Method for External Defibrillators," and U.S. Pat. No. 5,607,454, to Cameron et al. for "Electrotherapy Method and Apparatus," the entire contents of the specifications of which is incorporated herein by reference.

These defibrillator components communicate with each other over suitable communication buses, as shown.

External defibrillator 100 can be operated in different modes, such as self-test mode, stand-by mode, set-up mode, patient treatment mode, training mode and code-transfer mode. The operational characteristics of defibrillator 100 differ in each mode. In addition, the operational characteristics of the defibrillator in any one of the modes can be changed as explained below.

Operation of the external defibrillator of this embodiment commences with the insertion of a power supply 134 or user activation of the power on button. Once gate array 106 confirms that a power supply 134 is inserted, gate array 104 prompts MPU 102 to begin its boot sequence. The boot sequence begins with MPU 102 sending out a series of addresses to power supply 134.

As is known in the art, while in patient treatment mode, the defibrillator 100 typically (1) determines whether electrodes 137 are attached to electrode connector 136; (2) receives ECG information from a patient through such electrodes; (3) analyzes the ECG information to determine whether a therapeutic shock is advised; and (4) delivers a shock to the patient through the electrodes 137 if a shock is advised and if the shock button 126 is actuated by a user.

Figure 3:
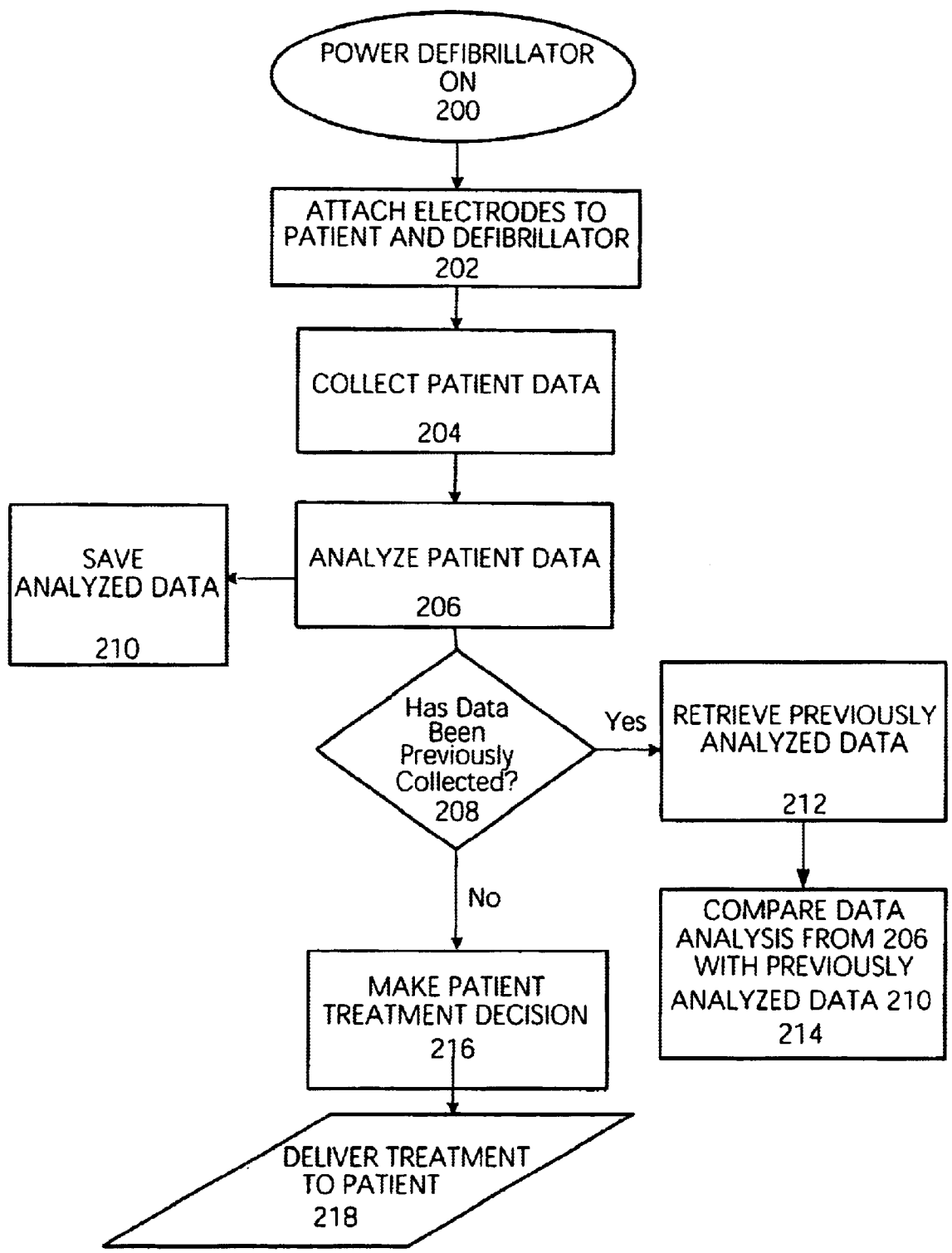
FIG. 3 represents a flow chart showing an embodiment of a method of operating the electrotherapy device according to the present invention.

Turning to FIG. 3, the method of operating the defibrillator according to the invention is shown. Defibrillator 10 has an adaptable electrotherapy diagnostic and treatment system ("AEDTS") incorporated in, for example, MPU 102. The AEDTS is used to adapt patient treatment based upon one or more prior events, algorithm decisions, analysis results, and/or protocol events.

Initially, the defibrillator is turned on 200. Once the defibrillator has been turned on the electrodes are attached to the patient at one end and the defibrillator at the other end 202. As will be appreciated by those of skill in the art, the step of attaching the electrodes could be performed prior to turning the defibrillator on 200. Alternatively, the step of attaching the electrodes to the defibrillator could be eliminated altogether where, for example, the electrodes are already connected to the defibrillator.

Once the defibrillator has been turned on and the electrodes have been attached to the patient and the defibrillator, the defibrillator can begin to monitor the patient data. Data is typically collected in a data segment over a specific time period 204. A suitable time period for a collected data segment would be, for example, 10 s. The collected data segment is then analyzed 206.

Prior to making a decision on whether to administer therapy to a patient based on the analysis of the data segment 206, the AEDTS determines whether data has previously been analyzed during the current treatment session 210, i.e., since the defibrillator was turned on 200. If data has been previously analyzed, the previously analyzed data is retrieved 212 and compared with the most recently analyzed data 214. As will be appreciated by those of skill in the art, more than one previously analyzed data segment may be retrieved at 214 and compared to the most recently analyzed data. Thus, a data segment may be compared to a plurality of prior data segments. More information regarding data segment analysis is available in copending application of David E. Snyder, et al. entitled "Circuit and Method for Analyzing A Patient's Heart Function Using Overlapping Analysis Windows," filed Jul. 13, 2000 and assigned U.S. Ser. No. 09/615,280, the entire contents of the specification of which is hereby incorporated herein by reference.

Following the comparison of the most recently analyzed data with the previously analyzed data 214 a patient treatment decision is made 216 and treatment is delivered to the patient 218, if appropriate. The effect of the comparison may result in a change in the treatment decision. For example, where a patient has a thrombosis in a coronary artery and a region of the heart is ischemic as a result of the thrombus, the patient is predisposed to VF. In this situation, an electric shock will defibrillate the heart, but because the thrombus is still present and ischemia continues, VF will recur quickly. The AEDTS system recognizes this pattern when comparing current data with prior data for the same patient and thus may recommend thrombolytic therapy to eliminate the cause of recurrence of VF prior to further defibrillation.

In another example, where the post-shock rhythm is unstable, the AEDTS may recommend delivery of anti arrhythmic drugs to stabilize the rhythm.

If no data has been previously analyzed during the current treatment session 210, then the AEDTS stores the analyzed data segment for future use 208. Following analysis of the data segment 206, a patient treatment decision is made 216 and treatment is delivered to the patient 218, if appropriate. As will be appreciated by those of skill in the art, the step of saving the analyzed data 210 may occur at any time following the analysis step 206. For purposes of illustration, the saving step 208 has been illustrated prior to the step of checking for previously analyzed data 210, however, the step could be performed at other times without departing from the scope of the invention.

The foregoing description of the invention illustrates and describes the present invention. Additionally, the disclosure shows and describes only the preferred embodiments of the invention, but as aforementioned, it is to be understood that the invention is capable of use in various other combinations, modifications, and environments and is capable of changes or modifications within the scope of the inventive concept as expressed herein, commensurate with the above teachings, and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed:

1. An electrotherapy device, comprising:
    at least one sensor operable to sense at least one physiological parameter of a patient;
    a controller operably connected to the at least one sensor operable to receive signals from the at least one sensor corresponding to the at least one physiological parameter;
    memory operable to store computer programming code executed by the controller, the programming code comprising decision-making criteria operable to adapt a patient treatment in response to changes to the detected at least one physiological parameter; and
    at least one pair of electrodes operably connected to the controller and operable to administer the treatment to the patient,
wherein the at least one physiological parameter comprises at least one of an ECG parameter and a heart rate parameter and the ECG parameter is selected from the group comprising conduction variable and stability variable
    a user interface operably connected with the controller and operable to enable a user to adapt the decision-making criteria of the programming code.

2. The electrotherapy device according to claim 1, wherein the decision-making criteria adapt patient treatment response by generating a shock/no-shock decision.

3. The electrotherapy device according to claim 1, wherein the decision-making criteria adapt patient treatment by generating a therapy decision.

4. The electrotherapy device according to claim 1, wherein the user interface comprises a tactile input device operably connected to the electrotherapy device.

5. The electrotherapy device according to claim 1, wherein the computer programming code is executed in the controller to recommend alternative patient therapies based on at least one of prior patient events and arrhythmia analysis algorithm decisions.

6. An electrotherapy device comprising:
    at least one sensor operable to sense at least one physiological parameter of a patient;
    a circuit operably connected to the sensor and configured to detect a patient physiological parameter; and
    a controller operably connected to the circuit and operable to receive signals from the circuit corresponding the to the at least one physiological parameter, the controller being configured to implement decision-making criteria responsive to changes in the measured parameter values, and operative to adapt patient treatment based upon the decision-making criteria,
    wherein the decision-making criteria utilize the at least one patient physiological parameter and a history of decision-making criteria.

7. The electrotherapy device according to claim 6, wherein the at least one patient physiological parameter comprises at least one of an ECG parameter and a heart rate parameter.

8. The electrotherapy device according to claim 7, wherein the EGG parameter is selected from the group comprising conduction variable and stability variable.

9. The electrotherapy device according to claim 6, wherein the at least one patient physiological parameter comprises a heart conduction variable.

10. The electrotherapy device according to claim 6, wherein the at least one patient physiological parameter comprises a heart stability variable.

11. The electrotherapy device according to claim 6, wherein the controller utilized the decision-making criteria to generate a shock/no-shock decision.

12. The electrotherapy device according to claim 6, wherein the controller utilizes the decision-making criteria to generate a therapy decision.

13. The electrotherapy device according to claim 12, wherein the sensor comprises a patient electrode and the circuit comprises a cardiac event detection system.

14. A method for performing electrotherapy using an external-body device, the method comprising:
    detecting at least one physiological parameter of a patient;
    analyzing the at least one physiological parameter;
    adapting a patient treatment in response to changes in the detected at least one physiological parameter;
    administering the treatment to the patient; and determining whether at least one prior physiological parameter has been analyzed;
    if at least one prior physiological parameter has been analyzed, evaluating the at least one prior physiological parameter in conjunction with the analyzed at least one physiological parameter and making a treatment decision based on the evaluation; or
    if at least one prior physiological parameter has not been analyzed, evaluating the analyzed at least one physiological parameter and making a treatment decision based on the evaluation.

15. The method according to claim 14, wherein analyzing the at least one physiological parameter comprises analyzing at least one of heart rate, heart condition, heart stability, blood pressure, and $SPO_2$.

16. A method for performing electrotherapy using an external-body device, the method comprising:
    detecting at least one physiological parameter of a patient;
    analyzing the at least one physiological parameter;
    adapting a patient treatment in response to changes in the detected at least one physiological parameter;
    administering the treatment to the patient;
    providing a circuit and a sensor operable to detect the at least one physiological parameter, and providing control circuitry operable to implement the decision-making criteria operable to adapt treatment based upon the decision-making criteria;

adapting a patient treatment comprising a defibrillating shock in response to analysis of at least one prior detected physiological parameter; and delivering the defibrillating shock to the patient with the control circuitry.

17. The method according to claim 16, wherein analyzing the at least one physiological parameter comprises analyzing at least one of heart rate, heart condition, heart stability, blood pressure, and $SPO_2$.

* * * * *